United States Patent [19]
Weber et al.

[11] Patent Number: 5,441,056
[45] Date of Patent: Aug. 15, 1995

[54] REPELLENT-TREATED, BARRIER-COATED NONWOVEN WEB

[75] Inventors: Robert E. Weber, Marietta; Steven W. Fitting, Acworth; Patricia A. Jegier, Marietta, all of Ga.

[73] Assignee: Kimberly-Clark Corporation, Neenah, Wis.

[21] Appl. No.: 193,965

[22] Filed: Feb. 9, 1994

Related U.S. Application Data

[62] Division of Ser. No. 616,133, Nov. 20, 1990, Pat. No. 5,370,132.

[51] Int. Cl.$^6$ ............................................. A41D 13/12
[52] U.S. Cl. ..................................... 128/849; 427/412; 428/308.4; 428/311.1; 428/315.9; 428/336; 428/907
[58] Field of Search ................... 128/849; 428/308.4, 428/311.1, 315.9, 336

[56] References Cited

U.S. PATENT DOCUMENTS

| | | | |
|---|---|---|---|
| 4,041,203 | 8/1977 | Brock et al. | 428/157 |
| 4,156,753 | 5/1979 | Tanaka | 427/245 |
| 4,411,928 | 10/1983 | Baldwin | 427/2 |
| 4,508,113 | 4/1985 | Malaney | 128/132 |
| 4,522,203 | 6/1985 | Mays | 128/132 |
| 4,713,068 | 12/1987 | Wang et al. | 604/366 |
| 4,713,069 | 12/1987 | Wang et al. | 604/378 |
| 4,758,239 | 7/1988 | Yeo et al. | 604/366 |
| 4,818,600 | 4/1989 | Braun et al. | 428/290 |
| 4,828,556 | 5/1989 | Braun et al. | 604/365 |
| 5,027,438 | 7/1991 | Schwarze et al. | 2/114 |
| 5,151,314 | 9/1992 | Brown | 428/198 |
| 5,183,664 | 2/1993 | Ansell | 424/445 |
| 5,183,702 | 2/1993 | Taylor et al. | 428/266 |
| 5,188,885 | 2/1993 | Timmons et al. | 428/198 |

FOREIGN PATENT DOCUMENTS 0177364  4/1986  European Pat. Off. .

*Primary Examiner*—James C. Cannon
*Attorney, Agent, or Firm*—William E. Maycock

[57] ABSTRACT

Disclosed herein is a repellent-treated, barrier coated nonwoven web. Nonwoven webs with small fiber and pore sizes can often be surface coated with a barrier coating such as latex to form a nonwoven which will act as a barrier to liquids. Surface coating of nonwovens having larger pores and fibers is more difficult as the coating often sinks into the thickness of the nonwoven web. The material of the present invention is a larger fiber/pore nonwoven web which will permit surface coating to form a material which has a good hand and cloth-like feel while also acting as a barrier to liquids. Such a material has a wide variety of applications including, but not limited to, personal care products, surgical drapes and gowns and other applications requiring barrier properties.

2 Claims, 5 Drawing Sheets

REPELLENT-TREATED, BARRIER-COATED NONWOVEN WEB

This application is a division of application Ser. No. 07/616,133 entitled "Repellent-Treated, Barrier Coated Nonwoven Web" and filed in the U.S. Patent and Trademark Office on Nov. 20, 1990, and now U.S. Pat. No. 5,370,132.

BACKGROUND OF THE INVENTION

The present invention relates to a nonwoven web of a distinct design which has been specially treated with a fluorocarbon or other repellent agent and then top-coated with a polymer coating which essentially coats the top of the nonwoven web to form a fluid impervious barrier without saturating the nonwoven web or batt.

Latex-saturated webs are well known. Nonwoven materials are frequently run through coating solutions such as in a dip-and-squeeze method and then allowed to dry, thereby forming a saturated nonwoven web which may have varying degrees of impermeability to liquids and gasses. While such saturation techniques are well suited for a number of end uses, they do in fact utilize a large amount of the saturant. This is particularly true if fluid barrier properties are only needed on one side of the nonwoven web. As a result, it is an object of the present invention to provide a nonwoven web which has a uniform coating on one surface of the nonwoven web, thereby reducing the amount of saturant or coating material needed to create a material which is fluid-impervious.

While there are a wide variety of nonwovens, many of which can be completely saturated, there are currently only a select few nonwoven materials that can be surface coated with a fluid-impervious layer such as latex. One example can be found in U.S. Pat. No. 4,818,600, which is commonly assigned to the assignee of record. This patent teaches the use of a coating of a polyacrylate (latex) on one surface of a microfibrous meltblown nonwoven web. Surface coating of this material is possible because of the fine fiber structure and small pore size of the meltblown material. These features of the nonwoven permit the coating to treat the surface and not substantially soak into the material as the fluid impervious polyacrylate layer is formed. A problem arises, however, when the surface coating of a larger fiber, more porous material such as a spunbond nonwoven is attempted. More often than not, spunbond materials have much larger fibers and larger pores than microfibrous meltblown materials. As a result, the same types of coatings that are used to coat meltblown nonwovens cannot always be used to surface coat spunbond or other larger fiber structures. This is because the coatings cannot bridge the gaps between the fibers; therefore, the coating penetrates into the interior regions of the nonwovens. Accordingly, it is another object of the present invention to provide a nonwoven structure utilizing larger fibers which can still be surface coated with a fluid-barrier coating such as latex. It is also an object of the present invention to provide a process for producing such materials. These and other objects of the present invention will become more apparent upon a further review of the following specification, drawings and claims.

SUMMARY OF THE INVENTION

The present invention relates to a repellent-treated and barrier-coated nonwoven material which has numerous applications. The substrate for the invention is a nonwoven web or batt made from a plurality of entangled fibers. A wide variety of fiber forming processes are now available for forming nonwovens. The nonwoven web of the present invention is not limited to any one formation process so long as the nonwoven batt has the requisite properties as outlined below.

Surface barrier coating of nonwovens is possible when the fiber size and pore size of the nonwoven web are sufficiently small. Meltblown materials which typically have fiber diameters less than 10 microns usually have very small pore structures and thus can be surface coated with coatings such as latex emulsions with little or no problem. This is because the pores or gaps between the fibers of the nonwoven batt adjacent the surface are sufficiently small so that the coating can bridge the gaps between the fibers thereby coating only the surface and forming a barrier layer to liquids.

Larger fiber nonwovens usually have larger pores or gaps between the fibers. As a result, without significantly increasing the solids content of the barrier coating, the larger fiber nonwoven webs cannot be effectively barrier coated without the coating soaking into the thickness of the nonwoven. While liquid barrier materials can be formed by completely soaking or saturating the nonwoven web, this is often expensive due to the amount of barrier coating used and the fact that the nonwoven web can become stiff and noncloth-like, a property not desired in clothing applications.

The material of the present invention comprises a plurality of entangled fibers which form a nonwoven batt having a top and button surface. The surface of the batt which is to be barrier coated (whether it be the top or bottom surface) includes fibers having average widths along their major axes which are greater than or equal to 10 microns. In additions, the surface pores between the fibers to be coated should have average diameters ranging from about 50 to about 100 microns. The fibers of the surface to be barrier coated are treated with a liquid repellent coating and then top-coated with a barrier coating to a thickness of about 37 microns or greater to form a liquid-repellent barrier material.

If desired, the batt can be bonded with a plurality of bond points having individual surface areas less than or equal to about 0.006 cm$^2$ to cover between about 10 and about 30 percent of the total surface area to be barrier coated. The repellent coating should be present in a range of about 0.3 to about 3.0 dry parts repellent coating per 100 parts fiber by weight. The barrier coating itself can have a glass transition temperature (Tg) in the range of about $-50°$ C. to about 30° C. with a preferred range being between about 0° C. to about 10° C. To further enhance to properties of the barrier coating, it may also contain a cross-linking agent as well as a repellent treatment. The coatings themselves can be made form such things as latexes and aqueous solution polymers. Once formed, the barrier material of the present invention will have a Gurley air porosity greater than or equal to 10,000 seconds. Such materials have a wide variety of applications, not the least of which include surgical and clean room supplies such as drapes, gowns and protective wear.

DESCRIPTION OF PREFERRED EMBODIMENT

Figure 1:
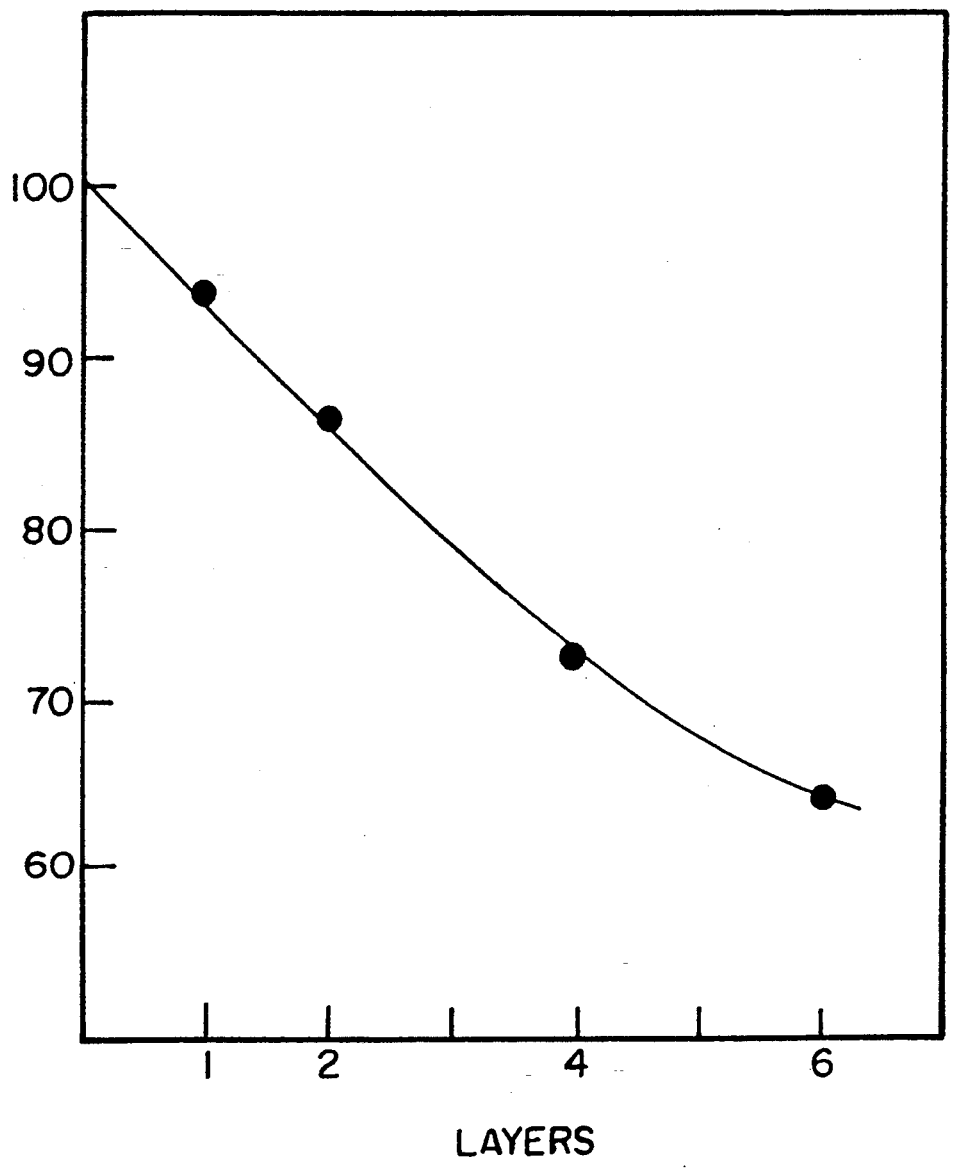
FIG. 1 is a plot of the mean pore diameter range of a nonwoven web suitable for use with the present invention.

The present invention relates to a nonwoven material which is a barrier to non-reactive liquids. More specifically, the material is a rather coarse fiber nonwoven which has been treated with a repellent and then surface-coated with a barrier coating to yield a fabric which has liquid barrier properties. Such barrier materials have a wide variety of uses including, but not limited to, health care and personal care products.

Nonwovens are continually being used as replacements for woven fabrics in a wide variety of applications. As the needs and uses of nonwovens increase, so too do the types of nonwovens and the methods for producing them. In certain applications, it is desirous to form nonwovens which act as barriers to various fluids, especially liquids, water, water-based liquids and body fluids such as blood and urine. Certain materials perform fairly well as repellent materials without barrier coatings. One example is a class of nonwoven materials generally referred to as polypropylene meltblown materials. These materials are made from very fine fiber structures with limited intersticial spacing and therefore small pores. Because of this fine fiber/small pore structure, such materials are capable of repelling liquids provided the hydrohead pressure is not excessive. One example of such a material is a laminate structure including two spunbond nonwoven layers separated by a meltblown nonwoven layer. Such a material is sold by the assignee of record, Kimberly-Clark Corporation, under the registered trademark "Evolution" fabric. This material is routinely used in such applications as the health care area for surgical drapes and gowns.

Larger fiber nonwovens, such as spunbond materials, do not have the barrier properties of smaller fiber nonwovens such as meltblown materials. As a result, for the most part spunbond materials are not used as barriers to liquids without further processing. This is because spunbond materials generally have larger fiber diameters and greater intersticial spacing thereby forming larger pores within the structure which will readily pass fluids such as water. One way to increase the barrier properties of spunbond and other larger pore structure nonwovens is to saturate them with a coating which when dried or cured fills the intersticial spacing between the fibers thereby forming the barrier-like properties in the material.

In the past, this barrier coating saturation technique has been one of the most common means for imparting barrier properties to porous nonwovens. A problem with this process, however, is the fact that a large amount of saturant, such as a latex material, must be used in the saturation process. From a cost standpoint, the more saturant that is used in forming the barrier material, the more expensive the material becomes from an end product standpoint. In many instances a surface coating, such as a latex, would suffice to impart sufficient barrier properties to the material. This is especially true when only one side of the end product will actually be subjected to fluid insults. Surface coating of such larger pore/fiber structures would provide an economic benefit to the overall cost of the material. Unfortunately, most barrier coatings are liquid in nature and do not have sufficient cohesive forces to enable the coatings to be coated on to the surface of the nonwoven structure and bridge the gaps or pores between fibers without sinking into the structure. Consequently, such coatings must either have such a high solids content that they are hard to process or, conversely, those coatings which are capable of running on high speed equipment sink into the nonwoven during the coating process and either saturate the material or fail to form a barrier across the entire surface area of the material. One exception to this is extrusion coating of the nonwoven, but in this case a material with very stiff undesirable property results.

The nonwoven web of the present invention includes fibers having average widths across their major axes greater than or equal to about 10 microns at least in the area which will be surface coated with a barrier coating. The fibers themselves can be made from any number of polymers and resins including, but not limited to, polyolefins, polyesters and polyamides. In addition, the fibers can have circular cross sections or shaped cross-sections such as "X", elliptical, star, bilobal, "H", trilobal or irregular configurations. When using non-circular cross-sections, the referenced width is measured along the major axis of the cross-section of the particular fiber shape.

The nonwoven batt of the present invention, once formed, may be bonded to impart additional integrity to the structure. Bonding may be by any number of means including ultrasonic and thermal pattern bonding as well as powder bonding. For purposes of the present invention, point bonding is preferred with the surface area of the individual bond points being less than or equal to about 0.006 cm$^2$. Furthermore, the total surface area of such bond points should be between about 10 percent and about 30 percent of the total surface area to be coated. Once the nonwoven has been formed, it is necessary for the pore structure to be such that the surface pores have average mean diameters ranging from about 50 to about 100 microns.

In order to be able to barrier coat a nonwoven batt having the surface pore and fiber sizes outlined above, the fibers forming the surface must be treated with a repellent coating material. While it is permissible to coat the entire fibrous structure with such a repellent coating, only the fibers adjacent the surface need to be treated to prevent the barrier coating from saturating the nonwoven web. Repellent coatings suitable for the present invention include those materials which do not adversely react with either the fibers of the web or the constituents which make up the barrier coating. Generally, the repellent coating should be a material which repels the liquid component of the barrier material being used. For example, if the barrier coating is an aqueous latex coating, then the repellent material should be one that repels water. Fluorocarbons are suitable repellents in this case. Other low surface energy resins such as silicones should also provide useful repellent properties. Addition of the liquid repellent coating material should be in the range of about 0.3 to about 3.0 dry parts repellent per 100 parts fiber by weight.

Once the fibers adjacent the surface to be barrier-coated have been treated, the barrier coating may be applied. Most of the barrier coatings will be added using an aqueous medium, latex being one example. The barrier material may be applied using any conventional means including, but not limited to, reverse roll coater, air knife and Mayer rod applications. Coating may be added in a single coat or in multiple coat applications but in either event it is desirable to have a coating thickness of about 37 microns or greater. Suitable barrier coatings include, but are not limited to polyacrylates, SBR, NBR, ABS, PVC and natural rubber latexes, as well as aqueous solution polymers such as polyethylene acrylic acid salts, polystyrene maleic acid salts, and polyacrylic acid salts. Such barrier coating materials will typically have a glass transition temperature (Tg) in the range of $-50°$ to $30°$ C. with a preferred range of about $0°$ to about $10°$ C. The transition temperature (Tg) is determined by DTA or DSC techniques in accordance with ASTM D-3418. Furthermore, a sufficient indication that are effective barrier has been achieved is if the barrier coated nonwoven web has a Gurley porosity greater than or equal to 10,000 seconds (100 cm$^3$ air for single sheet, see TAPPI test T460). To further strengthen the barrier coating and enhance the overall operation of the material of the present invention, it may be desirable to add a cross-linking agent to the barrier coating solution to cross-link the coating. If need be, repellent materials, such as fluorocarbons, also may be added to the barrier coating solution to enhance the product.

Generally it would be anticipated that the repellent coating on the nonwoven fibers would result in the nonwetting of the barrier coating to the fiber surface. But in the case of large diameter surface fibers and large pore spacings this normal condition does not exist and instead a uniform continuous barrier coating is formed. Conversely, when small fiber/pore structures, such as meltblowns, are repellent-created, they will not wet out and evenly coat with the barrier material.

EXPERIMENTATION

Web Structures

A series of experimental materials were made to determine what type of web structure could be surface-coated without the barrier coating substantially soaking into the structure of the web. One type of material tested was a spunbond-meltblown-spunbond material manufactured under the teachings of U.S. Pat. No. 4,041,203 to Brock et al., a patent commonly assigned to the assignee of record of the present invention. The first material tested comprised two 20 gram per square meter polypropylene ethylene copolymer spunbond webs laminated to opposite sides of an 8 gram per square meter polypropylene meltblown web. The first sample web material was fluorocarbon-treated with 0.4 parts Zepel ® 7040 (E. I. DuPont DeNemours and Company of Wilmington, Del.) per 100 parts fiber by weight. The sample was then calendered at $110°$ C. to reduce the average pore volume of the overall web from 79% to 55% while the size of the surface pores remained essentially the same. The second sample web material comprised two 16 g/m$^2$ polypropylene ethylene copolymer spunbond webs laminated to opposite sides of an 8 g/m$^2$ polypropylene meltblown web. This material was also calendered in the same manner to a pore volume of 43% but was not treated with a fluorocarbon. To calculate the percent pore volume of each of the samples, the apparent density of each sample was calculated by dividing the weight of the particular sample by its sample size (volume). The apparent density was then divided by the absolute density of the fiber polymer (a known value) and the quotient was then subtracted from the number one and that value was multiplied by 100 to yield the percent pore volume. The formula for this calculation is $(1 - dap/dab) \times 100\% = \%$ pore volume where dap is the apparent density and dab is the absolute density.

Both materials were then barrier-coated with an acrylic latex with a Tg of $+8°$ C. using a number 20 Mayer rod. The first sample which had been fluorocarbon-treated was uniformly surface-coated with the barrier coating material while the non-repellent-treated material had its coating soak into the thickness of the structure unlike the first sample where the coating stayed essentially on the surface.

In another experiment, two samples of a microfiber structure, in this case a Tyvek ® high density polyethylene web, style type 1079D from the E. I. DuPont DeNemours and Company of Wilmington, Del., were subjected to a similar test. Both samples were surface coated with an acrylic latex coating, however, only one of the samples was pre-treated with a fluorocarbon. In this case 4.2 milligrams of Zepel ® 7040 were added per 100 square centimeters of the Tyvek ® web. The latex coating had a Tg of $+8°$ C. Surprisingly, the web with the fluorocarbon treatment "fish-eyed" and would not wet out and evenly coat with the barrier coating material whereas the non-fluorocarbon treated material would take an even coat of the barrier material. Thus, it was determined that fluorocarbon treatment will only facilitate the uniform coating of nonwoven webs above a certain pore and fiber size.

To further verify the foregoing observations, additional testing was run on a number of materials with varying pore sizes, pore volumes, and fiber diameters. The coating results for such materials are shown in Table I. Based upon this testing, it can be seen that fine fiber structures, i.e., structures having pores sizes in the range of 12 to 18 microns and fiber diameters or major axes widths less than 10 microns will not uniformly surface coat when pre-treated with repellent coating. Conversely, in more open surface structures with fiber widths greater than about 10 microns and surface pores in the range of 50 to 100 microns (mean pore diameter as measured using a Coulter Porometer) a continuous uniform coating! of a barrier material could be applied. The mean surface ! pore diameter was measured using a Coulter ® Porometer from Coulter Electronics Limited, Luton, Beds. LU33RH England. This value was determined by measuring the mean pore flow diameter of one, two, four and six layers of nonwoven respectively placed in the sample holder of the measuring device. This data was then extrapolated to zero to establish the mean surface pore diameter. An example of this measurement of surface pore diameter is illustrated using a polyester nonwoven, Reemay ® 2010 from E. I. DuPont DeNemours and Company of Wilmington, Del. A plot of the mean flow pore diameter for this material is shown in FIG. 1.

enough they act the same as fluorocarbon treated fibers and a continuous coating over the entire web can be achieved. This has been demonstrated in Table II below with four different weld point sizes on a spunbond polyolefin surface batt material. It was found that if the weld points are about 0.006 cm² and less, almost all of bond points will be covered and a continuous coating layer can be formed.

TABLE II

| BOND PATTERN TYPE | WELD POINT SIZE (cm²) | COATING REMARKS |
|---|---|---|
| A | 0.0114 | Coating covered about 50% of weld points on web surface. |
| B | 0.0084 | Coating covered about 75% of weld points on web surface. |
| C | 0.0037 | Coating covered all weld points on web surface. |
| D | 0.0032 | Coating covered all weld points on web surface. |

TABLE I

| BATT | WEIGHT (g/m²) | FLUOROCARBON TREATED | MEAN SURFACE PORE DIAMETER COATED SIDE (μm) | PORE VOL. (%) | FIBER WIDTH COATED SIDE* (μm) | REMARKS - COATING PROPERTIES |
|---|---|---|---|---|---|---|
| Spunbond Polypropylene | 17 | FC 461 | 57 | 78 | 14.7 ± 1.0 11.7 — 16.4 | Uniform continuous film on surface. |
| Spunbond Polypropylene | 17 | None | 57 | 78 | 14.7 ± 1.0 11.7 — 16.4 | Coating soak-in, no film on surface. |
| Spunbond (SB) Meltblown (MB) Composite Polypropylene Ethylene Copolymer | 51 | Zepel ® 7040 | ≈57 | 79 | 37.9 ± 7.5 14.7 — 48.1 | Uniform continuous film on SB surface side. |
| Spunbond (SB) Meltblown (MB) Composite Polypropylene Ethylene Copolymer | 51 | Zepel ® 7040 | ≈18 | 79 | 37.9 ± 7.5 14.7 — 48.1 | No film, nonwetting of (MB) fibers by coating. |
| Spunbond Polypropylene | 68 | Zepel ® 7040 | 57 | 80 | 17.6 ± 1.1 15.7 — 19.2 | Uniform continuous film on surface. |
| Reemay ® 2010 Polyester | 27 | Zepel ® 7040 | 100 | 87 | 25.2 ± 1.1 22.7 — 39.8 | Film formed on surface, no coating soak-in. |
| Reemay ® 2010 Polyester | 27 | None | 100 | 87 | 25.2 ± 3.2 22.7 39.8 | Coating soak-in, no film on surface. |
| Spunbond-Meltblown Composite (Surface Fibers Co-Polymer Propylene Ethylene) | 48 | Zepel ® 7040 | ≈57 | 79 | 20.01 ± 4 17.4 — 22.6 | Uniform continuous film on surface. |
| Meltblown Polypropylene | 43 | None | 17.5 | 83 | 4 ± 2 | Uniform continuous coating on surface. |
| Meltblown Polypropylene | 43 | FC 461 | 17.5 | 83 | 4 ± 2 | No film, nonwetting surface by coating. |

*25 SEM measurements (average, std deviation, and range). Coating consisted of a polyacrylate with a Tg of +8° C. and the coating weights were varied between 30 and 60 g/m².

Bond Area

Many nonwoven batts are thermally or ultrasonically spot-welded over the entire web surface to provide strength to the material. Generally the welded area covers between 10 and 30% of the total web surface. When these weld points become too large and are fluorochemical-treated, it becomes difficult to form a continuous coating over these weld points because the weld points act like a fluorochemical-treated film which will not be wetted by the barrier coating. Therefore, coating skips occur at the weld points. This generally does not change the barrier properties of the coated web because the weld points are barrier seals in and of themselves. Nevertheless, the coating is not continuous. It has been found that if these weld points are small Repellent Treatment Having described the nature and characteristics of a nonwoven substrate suitable for the present invention, the repellent coating will now be described. Generally, the repellent coating will be either aqueous or solvent-based though aqueous solutions are more common. In either case the repellent coating can be added by any number of known methods. Dip and squeeze saturation and spraying are two such methods. Suitable repellent chemicals include but are not limited to fluorocarbons. Other low surface energy materials such as silicones should be useful.

Aqueous fluorocarbons were the preferred repellents used during the testing. Aqueous coatings were applied to the nonwoven batts as illustrated in Table I by either dip and squeeze saturation or spraying. The excess coating was removed with a nip squeeze roll and the batts were dried on heated rotating drums or a hot air oven at a temperature of about 107° C. The solution solids were generally in the range of 0.5 to 1.0 percent with the useful add-on of the fluorocarbon being in the range of 0.3 to 3.0 dry parts per 100 parts fiber by weight. Sources for such fluorocarbons include Zepel ® 7040 by Dupont of Wilmington, Del. and Textile Chemical FC-461 by CIBA-GEIGY of Greensboro, N.C. See Table III for more data regarding repellent add-on and its effect.

Barrier Coatings

The barrier coating should be a material which will uniformly coat the repellent-treated surface of the nonwoven batt and not substantially soak into the thickness of the batt. It has been found that the material of the present invention will have sufficient barrier properties to liquids when the barrier-coated material has a Gurley porosity greater than or equal to 10,000 seconds. Barrier coating materials are generally aqueous-based emulsions but solvent based systems should not be precluded. Aqueous latex systems have been found to be particularly useful with the present invention. A partial listing of such systems is shown in Table IV including the trade name, latex type, glass transition temperature and remarks with respect to the tactile and visual characteristics of the coated surface.

For most applications a completely non tacky feel is desired while still maintaining a soft flexible coating. This appears to be best accomplished with latexes having a glass transition temperature (Tg) in the range of 0° to 10° C. Above this level the coating techniques on a

TABLE III

| BATT | WEIGHT (g/m$^2$) | FLUOROCARBON TREATED ZEPEL ® 7040 PARTS/100 PARTS FIBER | PORE VOLUME (%) | FIBER WIDTH* ($\mu$m) | REMARKS - COATING PROPERTIES |
|---|---|---|---|---|---|
| Spunbond-Meltblown-Spunbond Composite (Surface Fibers Copolymer Propylene Ethylene) | 48 | 0.35 | 79 | 20.0 ± 1.4 17.4 — 22.6 | Uniform continuous film on surface. |
| Spunbond-Meltblown-Spunbond Composite (Surface Fibers Copolymer Propylene Ethylene) | 48 | 0.35 | 71 | 20.0 ± 1.4 17.4 — 22.6 | Uniform continuous film on surface. |
| Spunbond-Meltblown-Spunbond Composite (Surface Fibers Copolymer Propylene Ethylene) | 48 | 0.35 | 62 | 20.0 ± 1.4 17.4 — 22.6 | Uniform continuous film on surface. |
| Spunbond-Meltblown-Spunbond Composite (Surface Fibers Copolymer Propylene Ethylene) | 48 | 0.35 | 55 | 20.0 ± 1.4 17.4 — 22.6 | Uniform continuous film on surface. |
| Spunbond-Meltblown-Spunbond Composite (Surface Fibers Copolymer Propylene Ethylene) | 39 | None | 43 | 37.9 ± 7.5 14.7 — 48.1 | Coating soaks into open pores of composite, no film on surface. |
| Tyvek ® 10790 (High density polyethylene) | 76 | None | 60 | 4 | Uniform coverage by coating with approximately 50% soak in into the base. |
| Tyvek ® 10790 (High density polyethylene) | 76 | 0.5 | 60 | 4 | Complete nonwetting of base by coating, no film forming. |

*25 SEM measurements (average, std. deviation and range)
**Polyacrylate coating, Tg + 8° C., coating weights of approximately 50 g/m$^2$.

fluorocarbon treated surface fibers will work. At Tg less than 0° C., coatings are slightly tacky at room temperature and generally are sticky at elevated temperature. This can generally be corrected using post treatment of a light dusting of dry starch or talc.

Zepel® 7040 repellent per 100 parts fiber by weight. The first barrier coat was dried in a hot air oven at 107° C. until dry (about one minute) before the second coating was applied. The final coat weight for the material was 64 g/m² and the composite exhibited good barrier

TABLE IV

| TRADE NAME | LATEX TYPE | Tg (C.°) | REMARKS WITH REFERENCE TO COAT SURFACE CHARACTERISTICS |
|---|---|---|---|
| Hycar 157OX55 | Soft ABS | −48 | Slightly tacky, soft feel, glossy surface. |
| Hystretch V-29 | Elastic-Acrylic | −29 | Slight tacky, glossy surface. |
| Rhoplex HA-8 | Acrylic | −14 | Very tacky, sticks to self readily. |
| Dur-O-Set E-646 | Ethylene-Vinyl Acetate | −12 | Slightly tacky, soft feel, glossy surface. |
| Hycar 26120 | Acrylic | −11 | Slightly tacky, soft to touch surface. |
| Rhoplex NW 1715 | Acrylic | −9 | Slightly tacky, uniform coating coverage but barrier properties only moderately good. |
| Rhoplex B-15 | Acrylic | −4 | Slightly tacky, soft to the touch surface. |
| Geon 550 | PVC Plasticized with NBR latex | +4 | No tack, moderately soft surface. |
| Hycar 26084 | Acrylic | +8 | Very slight tack, moderately soft surface. |
| Hycar 26445 | Acrylic | +8 | No tack, soft feel, semi-gloss surface. |
| Hycar 26106 + | Styrene Acrylic | +29 | No tack, coating creases, hard coating surface, dull gloss. |
| Hartex 104 | Latex: Natural rubber latex blend (Ratio: 2:1) | −70 | |

Figure 2:
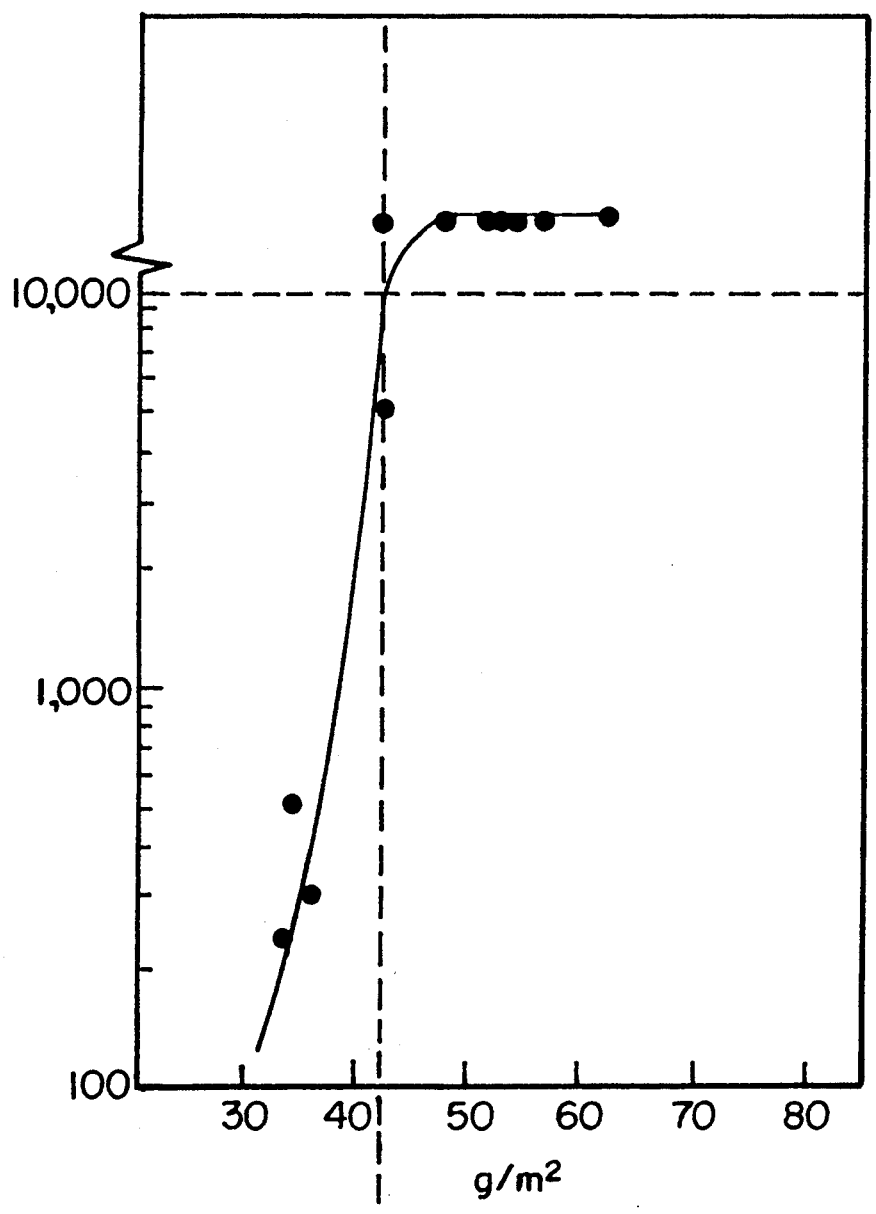
FIG. 2 is a plot of the barrier coating thickness necessary to achieve a Gurley porosity of at least 10,000 seconds per 100 cubic centimeters of air and thus create a liquid barrier material according to the present invention.

A minimum barrier coating thickness of about 37 microns is needed to develop a complete barrier on an open web structure as is shown in FIG. 2. The barrier properties appear to be independent of the number of coating layers necessary to reach the minimum barrier thickness of about 37 microns. For the data points shown in FIG. 2, double coats using a Mayer rod seem to work best when attempting to achieve low overall coat weights such as 43 grams of coating per square meter which is equivalent to a 37 micron thickness. In the case of single coatings only, it is best to increase the coating solids to achieve similar coating weights as compared to a double coating process. The latex used for the data points shown in FIG. 2 was an acrylic latex with a Tg of +8° C., an acid number of 9 and a film density of 1.15 g/cc. To reach a barrier with a single coat the coating weight had to be shifted from 43 g/m² to 50 g/m² or, in thickness, from 37 to 43.5 microns. A barrier is achieved when there is no air flow through the web using a Gurley Porometer. A Gurley value of 10,000 seconds or greater for a single web layer is judged as a no air flow condition. To achieve this, the aqueous coating solids for the acrylic latex were adjusted between the range of 30 to 45 percent depending upon whether single, double or triple coatings were used to achieve the barrier properties.

One preferred latex barrier coating formulation uses an acrylic latex and has the following formulation:

| Component | Weight |
|---|---|
| Hycar ® 26084 (acrylic latex with Tg (+8° C.) and acid #9) | 100 parts |
| NH₄OH to adjust the pH to 9.5 | |
| XAMA-7 (external cross-linking agent) | 5 parts |
| Ammonium oxalate (catalyst for cure) | 0.05 parts |
| QR-708 (viscosity modifier to adjust coating to 300 cps) | 1-2 parts |

The total solids by weight of the aqueous coating formulation were adjusted to 40 percent. This formulation was applied in two coats to one side of a 48 g/m² spunbond-meltblown-spunbond polypropylene composite web using a number 32 Mayer rod. The composite web, prior to barrier coating was pretreated with 0.4 parts of properties. In some cases, it is desirable to have additional water repellency added to the coated surfaces. In this case 5 parts of fluorocarbon chemical FC 461 can be added to the second coating. This does not change the barrier properties of the coating, but it does make aqueous solutions "bead up" on the surface, a desirable property for some applications such as hospital operating room gowns.

Another formulation useful as a barrier coating for the present invention employs the same above components but for a substitution of Hycar ® 26445 for the Hycar ® 26084 with all weight parts being the same. In addition, in this case the 48 g/m² spunbond-meltblown-spunbond polypropylene composite was pretreated with a 1% Zepel® 7040 solution by the dip and squeeze method to apply the fiber repellent coating. The web composite was dried at 107° C. for one minute. The fluorocarbon add-on was 3.0 parts per 100 parts fiber by weight. This web was then barrier coated with the above formulation composition.

It has also been found that solution polymers such as aqueous polyethylene acrylic acid salts (EAA) work equally well as latex systems in the coating of nonwoven batts containing large pores that have been pretreated with a fluorocarbon. One example of such a solution polymer utilizes a Primacor ® dispersion 4983 EAA from the Dow Chemical Company of Midland, Mich. which is a 25% aqueous ammonium solution of polyethylene acrylic acid with its pH adjusted to 9.5 with ammonium hydroxide (NH₄OH). To the EAA there is added one to two parts QR-708[1] to adjust the viscosity to a range of 300–400 centipoise (cps) and 0.5 parts of hexanol is added per one hundred parts EAA to assist in forming a uniform coating layer. This coating also worked well. A listing of some of the barrier materials and their sources is shown in Table V.

TABLE V

| SYNTHETIC LATEXES | |
|---|---|
| Polyacrylates | Hycar ® 26445, 26084, 26120, 26106, Hystretch ® V-19 B. F. Goodrich Company Cleveland, OH |
| | Rhoplex ® B-15, HA-8, NW-1715 |

TABLE V-continued

| | |
|---|---|
| Polyethylene vinylacetate | Rohm and Haas Company Philadelphia, PA Dur-O-Set ® E-646 National Starch & Chemical Co. Bridgewater, NJ |
| ABS rubber | Hycar 1570 × 55 B. F. Goodrich Company Cleveland, OH |
| Polyvinyl chloride, NBR blend | Geon ® 550 B. F. Goodrich Company Cleveland, OH |
| SOLUTION SYNTHETIC POLYMER | |
| Polyethylene acrylate | Primacon ® 4983 Dow Chemical Company Midland, MI |
| NATURAL LATEX POLYMER | |
| Natural Rubber (cis 1,4 polyisoprene | Hartex ® 104 Firestone Synthetic Rubber and Latex Co. Akron, OH |

[1] QR-708 is a thickening agent from Rohm and Haas Company of Philadelphia, Pennsylvania.

It has also been found that adding cross-linking agents to the barrier coating will help develop high solvent and water resistances. Either internal or external cross-linking agents can be used with the latex and solution polymer coatings. For example, external Cross-linking agents such as XAMA ® −7 and XAMA ® −2 (Virginia Chemicals of Portsmouth, Va.) can be used to cure the latex by reacting with the carboxyl functional characteristics of the latex. Internal cross-linking is also acceptable as with such polymers as Rhoplex ® B-15, HA-8 and NW-1715 and Hycar ® 26084 and 26120 where an elevated temperature is used to facilitate the cross-linking.

Lastly, coating viscosities should be in the range of 200 to 400 cps at solids concentrations of 25 to 45 percent. If need be, the viscosity of the coating can be adjusted by using a thickener such as Rohm and Haas QR-708.

Figure 3:
FIG. 3 is an electron photomicrograph of a repellent-treated spunbond nonwoven web successfully surface-coated with a barrier coating according to the present invention.
Figure 4:
FIG. 4 is an electron photomicrograph of an untreated spunbond nonwoven web which was unsuccessfully surface-coated with a barrier coating.

To visualize the effectiveness of the present invention, a series of electron photomicrographs were taken. These photomicrographs appear as FIGS. 3 through 8 of the drawings. FIG. 3 is a cross-sectional view of the first material described in Table I. This material was a spunbond polypropylene nonwoven having a basis weight of 17 gm/m². The nonwoven web was treated with a fluorocarbon and then coated with a polyacrylate coating. The material in FIG. 4 was also a 17 gram per square meter spunbond polypropylene nonwoven web, however, this material was not treated with a fluorocarbon prior to being coated with a polyacrylate coating. This was the second material described in Table I. As can be seen by comparing FIGS. 3 and 4, the fluorocarbon-treated nonwoven web was able to achieve a very smooth uniform coating across the top surface of the web while the material shown in FIG. 4 had its coating soak into the thickness of the web.

Figure 5:
FIG. 5 is an electron photomicrograph of a spunbond-meltblown composite nonwoven web successfully treated with a repellent and then barrier-coated according to the present invention.
Figure 6:
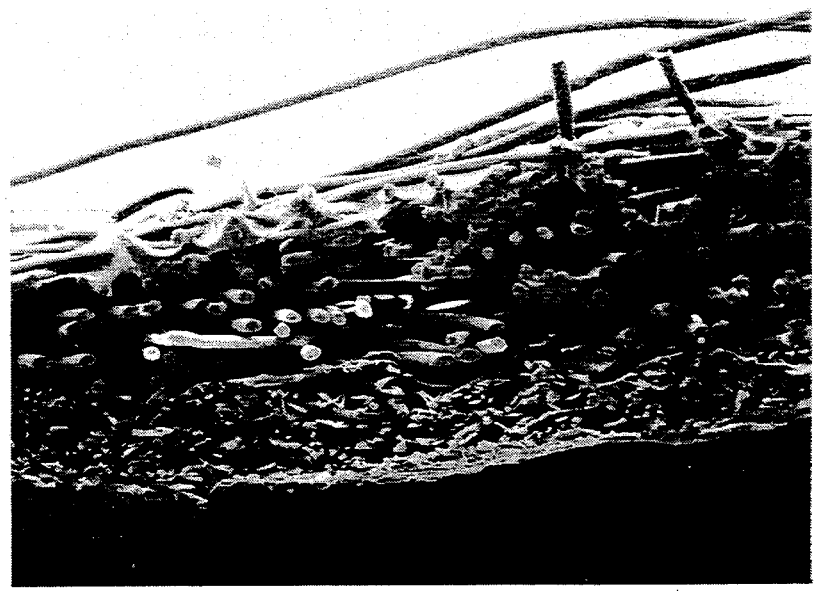
FIG. 6 is an electron photomicrograph of a spunbond-meltblown composite nonwoven web which was not repellent-treated and was unsuccessfully surface-coated with a barrier coating.

The material shown in FIG. 5 was the third material described in Table I. It consisted of a spunbond-meltblown composite nonwoven web having a basis weight of 51 grams per square meter. This material was treated with a fluorocarbon before coating with a polyacrylate coating. The material shown in FIG. 6 was the same as in FIG. 5 but was not treated with a fluorocarbon prior to its being coated with a polyacrylate coating. Once again it can be seen that the fluorocarbon-treated material (FIG. 5) was able to achieve a much better surface coating of the barrier material than was the nonfluorocarbon-treated material shown in FIG. 6.

Figure 7:
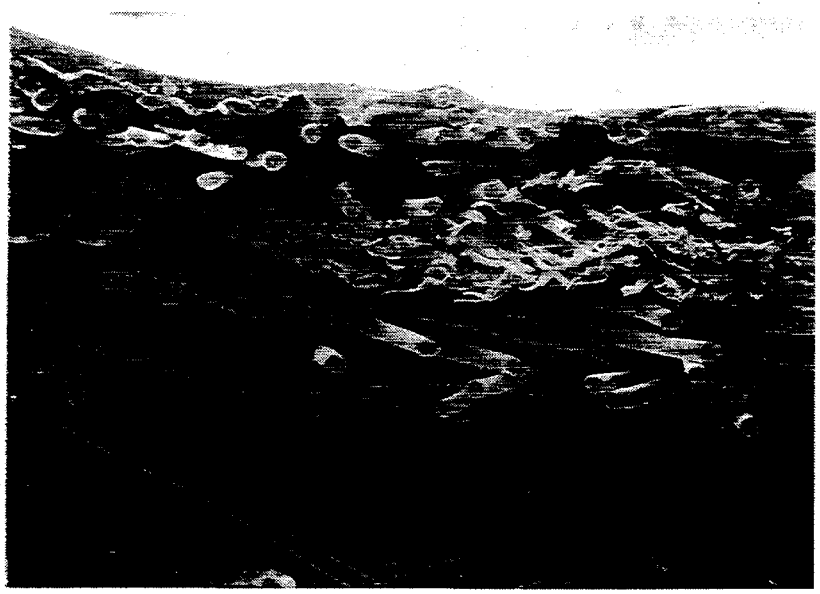
FIG. 7 is a electron photomicrograph of a spunbond-meltblown-spunbond composite nonwoven web as successfully treated with a repellent and then barrier-coated according to the present invention.
Figure 8:
FIG. 8 is an electron photomicrograph of a spunbond-meltblown-spunbond composite nonwoven web which was repellent-treated and was successfully surface-coated with a barrier coating.

The material shown in FIG. 7 150× magnification was a spunbond-meltblown-spunbond polypropylene composite having a basis weight of 48 g/m². This material was treated with Zepel ® 7040 fluorocarbon and coated with 64 g/m² of a polyacrylate coating. FIG. 8 is a photomicrograph of the same material having a magnification of 300×. Once again it can be seen that the surface coating is possible as a result of the repellent treatment prior to the barrier coating step.

Having thus described the invention in detail, it should be appreciated that various other modifications and changes can be made without departing from the spirit and scope of the following claims.

We claim:

1. A surgical drape including a liquid barrier material comprising:
   a plurality of entangled fibers forming a nonwoven batt, said batt having a top surface and a bottom surface, said top surface of said batt including fibers having average widths along their major axes greater than or equal 10 microns and surface pores in said top surface having average diameters ranging in size from about 50 to about 100 microns;
   a liquid repellent coating covering said fibers forming said top surface of said batt, and
   a barrier coating covering said top surface of said batt to form a liquid barrier, said barrier coating having a thickness of about 37 microns or greater.

2. A surgical gown including a liquid barrier material comprising:
   a plurality of entangled fibers forming a nonwoven batt, said batt having a top surface and a bottom surface, said top surface of said batt including fibers having average widths along their major axes greater than or equal 10 microns and surface pores in said top surface having average diameters ranging in size from about 50 to about 100 microns;
   a liquid repellent coating covering said fibers forming said top surface of said batt, and
   a barrier coating covering said top surface of said batt to form a liquid barrier, said barrier coating having a thickness of about 37 microns or greater.

* * * * *